United States Patent [19]

Sie

[11] Patent Number: 4,579,986

[45] Date of Patent: Apr. 1, 1986

[54] PROCESS FOR THE PREPARATION OF HYDROCARBONS

[75] Inventor: Swan T. Sie, Amsterdam, Netherlands

[73] Assignee: Shell Oil Company, Houston, Tex.

[21] Appl. No.: 717,066

[22] Filed: Mar. 26, 1985

[30] Foreign Application Priority Data

Apr. 18, 1984 [NL] Netherlands ................ 8401252

[51] Int. Cl.$^4$ .............................................. C07C 1/04
[52] U.S. Cl. ..................................... 585/324; 208/108;
  208/110; 208/113; 208/950; 518/704; 518/715;
  585/310; 585/469; 585/638; 585/648; 585/653;
  585/661
[58] Field of Search ............... 208/108, 110, 113, 116,
  208/950, 121; 518/704, 715; 585/310, 319, 324,
  329, 469, 638, 648, 653, 654, 661

[56] References Cited

U.S. PATENT DOCUMENTS

| | | | |
|---|---|---|---|
| 2,768,225 | 10/1956 | Moore | 585/653 |
| 3,433,851 | 3/1969 | Keblys | 585/654 |
| 4,410,637 | 10/1983 | Kortbeck et al. | 518/714 |
| 4,522,939 | 6/1985 | Minderhoud et al. | 502/242 |

OTHER PUBLICATIONS

Kirk-Othmer, "Encyclopedia of Chemical Technology", vol. 11, 3rd ed., (John-Wiley), pp. 473-478, (1980).

*Primary Examiner*—John Doll
*Assistant Examiner*—A. Pal

[57] ABSTRACT

Syngas is subjected to Fischer-Tropsch synthesis over a Co/Zr/SiO$_2$ catalyst and the C$_{20}$$^+$ fraction of the synthesized product is converted into linear C$_{10}$-C$_{20}$ olefins by mild thermal cracking.

11 Claims, No Drawings

PROCESS FOR THE PREPARATION OF HYDROCARBONS

FIELD OF THE INVENTION

The invention relates to a process for the preparation of linear olefins having at least 10 and at most 20 carbon atoms per molecule.

BACKGROUND OF THE INVENTION

Linear olefins having at least 10 and at most 20 carbon atoms per molecule (hereinafter referred to as "linear $C_{10}$–$C_{20}$ olefins") are valuable starting materials for the preparation of synthetic detergents. Said olefins can be obtained by mild thermal cracking of mixtures of linear paraffins having at least 20 carbon atoms per molecule (hereinafter referred to as "linear $C_{20}{}^+$ paraffins"). Linear $C_{20}{}^+$ paraffins, together with branched $C_{20}{}^+$ paraffins are found in heavy mineral oil fractions, such as lubricating oil fractions. The paraffins can be separated from said mineral oil fractions by cooling. From the paraffin mixtures obtained the desired linear paraffins can be isolated by way of fractional crystallization or complexing with urea. The linear $C_{20}{}^+$ paraffins thus obtained are generally contaminated with sulphur- and nitrogen compounds from the mineral oil, as well as cyclic compounds. Preparatory to being suitable for use as feed for the preparation of linear $C_{10}$–$C_{20}$ olefins by mild thermal cracking the $C_{20}{}^+$ paraffins should be freed from these contaminants.

Linear $C_{20}{}^+$ paraffins which can suitably be used as starting material for the preparation of linear $C_{10}$–$C_{20}$ olefins by way of mild thermal cracking may also be synthesized starting from a mixture of carbon monoxide and hydrogen. In this what is called Fischer-Tropsch synthesis a $H_2$/CO mixture is contacted at elevated temperature and pressure with a catalyst comprising one or more metals from the iron group together with one or more promoters and a carrier material. The preparation of these catalysts can suitably be carried out by the known techniques, such as precipitation, impregnation, kneading and melting. As compared with waxy heavy mineral oil fractions the products prepared by the Fischer-Tropsch synthesis have the advantage that they contain virtually no sulphur- and nitrogen compounds and cyclic compounds. Nevertheless the use of the products obtained over the usual Fischer-Tropsch catalysts for the preparation of linear $C_{10}$–$C_{20}$ olefins has two drawbacks which are connected with their composition. In the first place, these products contain but a relatively small amount of $C_{20}{}^+$ compounds as compared to the quantities of $C_{19}{}^-$ compounds present. Furthermore, the $C_{20}{}^+$ compounds are made up to a considerable extent of branched paraffins, branched and unbranched olefins and oxygen-containing compounds.

Recently there has been found a class of Fischer-Tropsch catalysts which have the property of yielding a product in which considerably more $C_{20}{}^+$ compounds are present than in the products prepared by the usual Fischer-Tropsch catalysts, which $C_{20}{}^+$ compounds consist virtually exclusively of linear paraffins. The Fischer-Tropsch catalysts belonging to the above-mentioned class contain silica, alumina or silica-alumina as carrier materials, and cobalt together with zirconium, titanium and/or chromium as catalytically active metals, in such quantities that per 100 pbw of carrier material the catalysts comprise about 3–60 pbw of cobalt and about 0.1–100 pbw of zirconium, titanium, and/or chromium. The catalysts are prepared by depositing the metals involved on the carrier material by kneading and/or impregnation. For further information concerning the preparation of these catalysts by kneading and/or impregnation reference may be made to Netherlands Patent Application No. 8301922, which is commonly assigned copending application, Ser. No. 594618, filed Mar. 29, 1984, now U.S. Pat. No. 4,522,939, issued June 11, 1985. Considering the composition of the product prepared over the cobalt catalysts, it is extremely attractive to separate from the product a heavy fraction substantially consisting of $C_{20}{}^+$ paraffins and to convert at least part of this heavy fraction by mild thermal cracking into a mixture of hydrocarbons substantially consisting of linear olefins and containing the desired $C_{10}$–$C_{20}$ olefins.

SUMMARY OF THE INVENTION

The present patent application therefore relates to a process for the preparation of linear $C_{10}$–$C_{20}$ olefins, in which a mixture of carbon monoxide and hydrogen is converted into a mixture of hydrocarbons substantially consisting of linear paraffins by contacting it at elevated temperature and pressure with a catalyst comprising about 3–60 pbw of cobalt and about 0.1–100 pbw of at least one other metal chosen from the group formed by zirconium, titanium and chromium per 100 pbw of silica, alumina or silica-alumina carrier, which catalyst has been prepared by kneading and/or impregnation, in which from the paraffin mixture thus prepared a heavy fraction is separated which consists substantially of $C_{20}{}^+$ paraffins, and in which at least this heavy fraction is converted by mild thermal cracking into a mixture of hydrocarbons which consists substantially of linear olefins and contains the desired $C_{10}$–$C_{20}$ olefins.

DESCRIPTION OF THE PREFERRED EMBODIMENTS

In the process according the the invention the starting material should be a $H_2$/CO mixture. Suitable $H_2$/CO mixtures can be prepared by the gasification of heavy carbonaceous materials, such as coal and residual mineral oil fractions. It is preferred to start from a $H_2$/CO mixture which has been obtained by the steam reforming or partial oxidation of light hydrocarbons, in particular natural gas.

In the process according to the invention preference is given to the use of the cobalt catalysts which form the subject matter of Netherlands Patent Application No. 8301922, which is commonly assigned co-pending application, Ser. No. 594618, filed Mar. 29, 1984, now U.S. Pat. No. 4,522,939, issued June 11, 1985. They are catalysts which satisfy the relation:

$$(3+4R) > L/S > (0.3+0.4R),$$

wherein

L = the total quantity of cobalt present on the catalyst, expressed as mg Co/ml catalyst, S = the surface area of the catalyst, expressed as $m^2$/ml catalyst, and R = the weight ratio of the quantity of cobalt deposited on the catalyst by kneading to the total quantity of cobalt present on the catalyst.

In the process of the invention use is further preferably made of cobalt catalysts which have been prepared by one of the three procedures mentioned hereinafter:
(a) first cobalt is deposited in one or more steps by impregnation and subsequently the other metal is deposited in one or more steps, also by impregnation,
(b) first the other metal is deposited in one or more steps by impregnation and subsequently the cobalt is deposited in one or more steps, also by impregnation, and
(c) first cobalt is deposited in one or more steps by kneading and subsequently the other metal is deposited in one or more steps by impregnation.

In the process according to the invention use is further preferably made of cobalt catalysts containing about 15-50 pbw of cobalt per 100 pbw of carrier. The preferred quantity of other metal present in the cobalt catalysts depends on the way in which this metal has been deposited. In the case of catalysts where first cobalt has been deposited on the carrier, followed by the other metal, preference is given to catalysts containing about 0.1-5 pbw of the other metal per 100 pbw of carrier. In the case of catalysts where first the other metal has been deposited on the carrier, followed by the cobalt, preference is given to catalysts containing about 5-40 pbw of the other metal per 100 pbw of carrier. Preference is given to zirconium as the other metal and to silica as carrier material.

In the process according to the invention the conversion of the $H_2/CO$ mixture is preferably carried out at a temperature of about 125°-350° C. and a pressure of about 5-100 bar and in particular at a temperature of about 175°-275° C. and a pressure of about 10-75 bar. The mild thermal cracking which according to the invention is applied to at least part of the heavy fraction of the product prepared over the cobalt catalyst is preferably carried out in the presence of steam. Further the mild thermal cracking is preferably carried out at a temperature of about 535°-675° C., a pressure of about 1-5 bar abs., a residence time of about 0.5-15 seconds and in the presence of a quantity of steam which is at most about 40 %w, calculated on the hydrocarbon feed, and in particular at a temperature of about 540°-600° C., a residence time of about 2-10 seconds and in the presence of a quantity of steam of about 3-20 %w, calculated on the hydrocarbon feed.

In the process according to the invention the product obtained by mild thermal cracking consisting substantially of linear olefins is divided into a light $C_9^-$ fraction, the $C_{10}-C_{20}$ fraction desired as end product, and a heavy $C_{21}^+$ fraction. The yield of linear $C_{10}-C_{20}$ olefins may be increased by recycling at least part of the heavy $C_{21}^+$ fraction to the mild thermal cracking, or by dividing the light $C_9^-$ fraction into a $C_4^-$ fraction and a $C_5-C_9$ fraction, subjecting at least part of the latter fraction, together with at least part of the heavy $C_{21}^+$ fraction to a combination of isomerization and disproportionation in order to prepare a mixture of linear olefins, and separating from the olefin mixture thus obtained an additional quantity of $C_{10}-C_{20}$ linear olefins. From the $C_4^-$ fraction which remains after the separation of the $C_9^-$ fraction, there can be separated ethene, from which linear olefins can be prepared by oligomerization, part of which linear olefins consist of $C_{10}-C_{20}$ olefins. The $C_9^-$ and $C_{21}^+$ olefins present in the mixture can be converted by means of the aforementioned combination of isomerization and disproportionation into a mixture of linear olefins from which $C_{10}-C_{20}$ olefins can be separated.

In the process according to the invention a further increase of the yield of linear $C_{10}-C_{20}$ olefins can be realized starting from the $C_{19}^-$ fraction obtained in the hydrocarbon synthesis over the cobalt catalyst, or from lighter fractions separated therefrom. By subjecting these fractions, which consist substantially of linear paraffins to steam cracking, a mixture of lower olefins can be obtained which consists substantially of ethene. The ethene can be oligomerized to prepare a mixture of linear olefins which consists partly of $C_{10}-C_{20}$ olefins. The $C_9^-$ and $C_{21}^+$ olefins formed in the oligomerization can be converted by the afore-mentioned combination of isomerization and disproportionation into a mixture of linear olefins from which the desired $C_{10}-C_{20}$ olefins can be separated. An increase of the yield of linear $C_{10}-C_{20}$ olefins, starting from the $C_{19}^-$ fraction obtained in the hydrocarbon synthesis over the cobalt catalyst, can also be realized by separating from the $C_{19}^-$ fraction a heavy fraction and subjecting it to dehydrogenation or chlorination, followed by dehydrochlorination. From the $C_{10}-C_{19}$ or the $C_5-C_9$ fraction of the product obtained over the cobalt catalyst can thus be prepared linear $C_{10}-C_{19}$ or $C_5-C_{19}$ olefins. The $C_5-C_{19}$ olefins present in the mixture of $C_5-C_{19}$ olefins can suitably be used as feed components in the disproportionation mentioned hereinbefore. The afore-mentioned processes for the preparation of linear $C_{10}-C_{20}$ olefins, starting from the $C_{19}^-$ fraction obtained in the hydrocarbon synthesis over the cobalt catalyst, can very suitably be combined by dividing the $C_{19}^-$ fraction into a light and a heavy fraction (for instance a $C_4^-$ and a $C_5-C_{19}$ fraction, or a $C_9^-$ and a $C_{10}-C_{19}$ fraction), and converting the light fraction by steam cracking/oligomerization and the heavy fraction by dehydrogenation or chlorination/dehydrochlorination.

In the present patent application there has thus far only been mention of the use of the product obtained over the cobalt catalyst as feed for the preparation of linear $C_{10}-C_{20}$ olefins. According to the invention, to this end at least part of the $C_{20}^+$ fraction should be subjected to mild thermal cracking. Optionally the entire $C_{20}^+$ fraction may be converted in this way. In addition, as described hereinbefore, part or all of the $C_{19}^-$ fraction can be used for the preparation of linear $C_{10}-C_{20}$ olefins. In view of the special composition of the product obtained over the cobalt catalyst which consists virtually entirely of linear paraffins, this product is also excellently suitable for a number of other applications, which can be combined with the process according to the invention. To this end use may be made either of part of the $C_{20}^+$ fraction or of at least part of the $C_{19}^-$ fraction.

In addition to its use according to the invention as feed for the preparation of linear $C_{10}-C_{20}$ olefins by mild thermal cracking, the $C_{20}^+$ fraction is very suitable for the uses following:
(1) Valuable solid paraffins can be separated from the $C_{20}^+$ fraction by fractional crystallization.
(2) A mixture of lower olefins substantially consisting of ethene can be obtained from the $C_{20}^+$ fraction by steam cracking.
(3) A product from which a lubricating oil with a high viscosity index can be obtained from the $C_{20}^+$ fraction by catalytic hydroisomerization.
(4) The $C_{20}^+$ fraction can be converted into middle distillates by catalytic hydrocracking.

In addition to its use as feed for the preparation of linear $C_{10}$-$C_{20}$ olefins the $C_{19}^-$ fraction is very suitable for the uses following:

(1) A mixture of lower olefins substantially consisting of ethene can be obtained from the $C_{19}^-$ fraction by steam cracking.
(2) By treating the $C_{10}$-$C_{19}$ fraction at an elevated temperature with a peroxide of the general formula R—O—O—$R^1$, wherein R and $R^1$ represent alkyl, aryl or acyl groups, said fraction can be converted into a product from which a lubricating oil with a high viscosity index can be separated.
(3) Certain fractions with a narrow boiling range which are present in the $C_5$-$C_{11}$ fraction can be suitably used as special solvents either such as they are or after a mild hydrogenation or hydroisomerization carried out to convert minor amounts of olefins and/or oxygen-containing compounds, or to introduce some branching. In this connection may be mentioned extraction liquors for oil seeds, spraying oils for insecticides and pesticides and as solvents for medicinal and pharmaceutical uses and in the food-stuff industry.

The afore-mentioned steam cracking for the preparation of a mixture of lower olefins substantially consisting of ethene may very suitably be carried out at a temperature of about 700°–1000° C., a pressure of about 1–5 bar abs., a residence time of about 0.04–0.5 seconds and in the presence of a quantity of steam which amounts to about 20–100 %w, calculated on hydrocarbon feed.

The invention is illustrated with the aid of the following example which is intended for illustration and not to be construed as limiting the invention.

EXAMPLE

Five hydrocarbon synthesis experiments were carried out by using the following catalysts.

Catalyst A

This catalyst comprised 10 pbw of iron, 5 pbw of copper, 2 pbw of potassium and 30 pbw of kieselguhr, and had been prepared by precipitation of iron and copper from an aqueous solution by using potassium carbonate, while kieselguhr was being added.

Catalyst B

This catalyst comprised 97.5 pbw of iron, 2.5 pbw of aluminum and 0.5 pbw of potassium, and had been prepared by melting a mixture of $Fe_3O_4$ and the oxides of aluminum and potassium in an arc.

Catalyst C

This catalyst comprised 100 pbw of cobalt, 5 pbw of thorium oxide, 7.5 pbw of magnesium oxide and 200 pbw of kieselguhr, and had been prepared by precipitation of cobalt and thorium from an aqueous solution, while kieselguhr was being added.

Catalyst D

This catalyst comprised 25 pbw of cobalt and 0.9 pbw of zirconium per 100 pbw silica, and had been prepared by kneading a silica carrier in a solution of cobalt nitrate in water, followed by single-step impregnation of the cobalt-loaded carrier with a solution of zirconylchloride in water.

Catalyst E

This catalyst comprised 23 pbw of cobalt and 17 pbw of zirconium per 100 pbw of silica, and had been prepared by three-step impregnation of a silica carrier with solution of zirconiumtetra n-propoxide in a mixture of n-propanol and benzene, followed by single-step impregnation of the zirconium-loaded carrier with solution of cobalt nitrate in water.

During the preparation of Catalysts D and E, such a quantity of solution was used in each impregnation step that its volume corresponds substantially with the pore volume of the carrier. After each impregnation step the solvent was removed by heating and the material was calcined at 500° C. When a kneading step was used, the quantity of solution used had a volume substantially corresponding with 150% of the pore volume of the carrier. When a kneading step was used, the mixture was kneaded in a kneading machine for three hours. During the kneading a small portion of the solvent was removed by heating. After the kneading step the paste obtained was recovered from the kneading machine, the remainder of the solvent was removed by heating, and the material was ground and calcined at 500° C.

Hydrocarbon synthesis experiments (1–5)

After Catalysts A–E had been activated by means of treatment with a hydrogen-containing gas at 250° C. they were used in the preparation of hydrocarbons from a mixture of carbon monoxide and hydrogen. The experiments were carried out in a reactor containing a fixed catalyst bed. The conditions under which the experiments were carried out and the results of these experiments are given in Table I. Of these experiments only Experiments 4 and 5 are part of the invention. Experiments 1–3 fall outside the scope of the invention. They have been included in the patent application for comparison.

Cracking experiment (6)

The $C_{20}^+$ fraction of the product prepared in accordance with Experiment 4 was cracked in the presence of steam at a temperature of 575° C., a pressure of 1 bar, a space velocity of 3.2 kg.$1^{-1}$.$h^{-1}$, calculated on the volume of the cracking zone, a steam dose rate of 6.5 %w, calculated on feed and a nominal residence time in the cracking zone of 2.5 seconds. After cooling and separation of the condensed water a product was obtained of which 5 %w consisted of a gas fraction, 14 %w of a light liquid fraction substantially boiling below 300° C., and 81 %w of a residual fraction substantially boiling above 300° C. The gas fraction obtained in the cracking was made up of hydrogen and light hydrocarbons. The cracking gas comprised 35 %v ethene and 17%v propene. The light liquid fraction consisted substantially of linear $C_5$-$C_{20}$ olefins. The olefins content was 95% and the α-olefins content 90%.

Cracking experiment (7)

The $C_5$-$C_9$ fraction of the product prepared according to experiment 4 was cracked in the presence of steam at an average temperature of 760° C., an average pressure of 1.5 bar, a residence time of 0.5 seconds and a steam/hydrocarbon weight ratio of 0.5. The composition of the product obtained is as given in Table II.

TABLE I

| Experiment No. | 1 | 2 | 3 | 4 | 5 |
|---|---|---|---|---|---|
| Catalyst No. | A | B | C | D | E |
| Temperature, °C. | 23 | 320 | 190 | 220 | 204 |
| Pressure, bar | 20 | 20 | 1 | 20 | 20 |
| $H_2/CO$ volume ratio | 1.7 | 2.5 | 2.0 | 2.0 | 3.0 |
| Space velocity, $Nl.l^{-1}.h^{-1}$ | 1750 | 1750 | 75 | 500 | 900 |
| Conversion $H_2 + CO$, % v | 22 | 30 | 70 | 75 | 62 |
| Product distribution, % w | | | | | |
| Gas ($C_1$-$C_4$) | 22.6 | 54.1 | 28.5 | 18.0 | 23.0 |
| Gasoline ($C_5$-200° C.) | 28.3 | 31.9 | 42.5 | 15.1 | 19.0 |
| Kerosine + gasoil (200-350° C.) | 19.5 | 2.5 | 19.5 | 28.4 | 22.4 |
| Waxy residue (350° C.$^+$) | 26.4 | 0 | 8.0 | 38.0 | 35.4 |
| Water-soluble oxygen compounds | 3.4 | 11.3 | 1.5 | 0.5 | 0.2 |
| Properties of $C_5^+$ product | | | | | |
| Olefins content, % mol | 50 | 80 | 34 | 8 | 2 |
| Aromatic content, % mol | 0.3 | 5.0 | 0.1 | 0 | 0 |
| Linearity, % (percentage linear paraffins and olefins calculated on total of paraffins and olefins) | 90 | 50 | 60 | 95 | 97 |
| Number of C atoms in tertiary structure, % | 1 | 5 | 4 | 0.2 | 0.1 |

TABLE II

| Composition in % w of product prepared according to Experiment 7 | |
|---|---|
| Hydrogen | 1 |
| Methane | 14 |
| Ethane | 5 |
| Ethene | 40 |
| Propane | 0.5 |
| Propene | 14 |
| $C_4$ | 8 |
| $C_5$ | 5 |
| $C_6^+$ | 12 |

I claim:

1. A process for the preparation of linear $C_{10}$-$C_{20}$ olefins, which comprises preparing a mixture of hydrocarbons substantially consisting of linear paraffins by:
   (a) Contacting a mixture of carbon monoxide and hydrogen at elevated temperature and pressure with a catalyst comprising 3-60 pbw of cobalt and 0.1-100 pbw of at least one other metal chosen from the group formed by zirconium, titanium and chromium per 100 pbw of silica, alumina or silica-alumina carrier, which catalyst has been prepared by kneading and/or impregnation,
   (b) Separating from the paraffin mixture thus prepared a heavy fraction which consists substantially of $C_{20}^+$ paraffins, and
   (c) Converting at least this heavy fraction by mild thermal cracking into a mixture of hydrocarbons which consists substantially of linear olefins and contains the desired $C_{10}$-$C_{20}$ olefins.

2. The process of claim 1, wherein a $H_2/CO$ mixture is used which has been obtained, starting from light hydrocarbons, by steam reforming or partial oxidation.

3. The process of claim 1, wherein $H_2/CO$ mixture is used which has been obtained starting from natural gas.

4. The process of claim 1, wherein a cobalt catalyst is used which satisfies the relation $$(3+4R) > L/S > (0.3 + 0.4R),$$

wherein
   $L$ = the total quantity of cobalt present on the catalyst, expressed as mg Co/ml catalyst,
   $S$ = the surface area of the catalyst, expressed as $m^2$/ml catalyst, and
   $R$ = the weight ratio of the quantity of cobalt deposited on the catalyst by kneading to the total quantity of cobalt present on the catalyst.

5. The process of claim 1, wherein a cobalt catalyst is used which, per 100 pbw of carrier, comprises 15-50 pbw of cobalt and either 0.1-5 pbw of the other metal when during the preparation cobalt was deposited first and the other metal next, or 5-40 pbw of the other metal when during the preparation the other metal was deposited first and the cobalt next.

6. The process of claim 1, wherein a cobalt catalyst is used which comprises zirconium as other metal and silica as carrier.

7. The process of claim 1, wherein step (a) is carried out at a temperature of 125°-350° C. and a pressure of 5-100 bar.

8. The process of claim 1, wherein step (a) is carried out at a temperature of 175°-275° C. and a pressure of 10-75 bar.

9. The process of claim 1, wherein the mild thermal cracking of the heavy fraction of the product prepared over the cobalt catalyst is carried out in the presence of steam.

10. The process of claim 1, wherein the mild thermal cracking is carried out at a temperature of 535°-675° C., a pressure of 1-5 bar abs., a residence time of 0.5-15 seconds and in the presence of a quantity of steam which amounts to at most 40 %w, calculated on the hydrocarbon feed.

11. The process of claim 1, wherein the mild thermal cracking is carried out at a temperature of 540°-600° C., a residence time of 2-10 seconds and in the presence of a quantity of steam which amounts to 3-20 %w, calculated on the hydrocarbon feed.

* * * * *